United States Patent [19]

Shigetomi et al.

[11] Patent Number: 4,647,194
[45] Date of Patent: Mar. 3, 1987

[54] DEVICE FOR JUDGING BRILLIANCY OF PRECIOUS STONES SUCH AS DIAMONDS OR THE LIKE

[75] Inventors: Tsuyoshi Shigetomi, Saitama; Kazuo Inoue, Kanagawa, both of Japan

[73] Assignee: J.P. M. Ltd. Co., Tokyo, Japan

[21] Appl. No.: 625,803

[22] Filed: Jun. 28, 1984

[30] Foreign Application Priority Data

Dec. 27, 1983 [JP] Japan .............. 58-205012[U]

[51] Int. Cl.⁴ .................................. G01N 21/87
[52] U.S. Cl. ........................................... 356/30
[58] Field of Search ................................. 356/30

[56] References Cited

U.S. PATENT DOCUMENTS

| 1,744,485 | 1/1930 | Michel et al. | 356/30 |
| 2,494,078 | 1/1950 | Woodruff | 356/30 |
| 2,742,813 | 4/1956 | Zeininger | 356/30 X |

FOREIGN PATENT DOCUMENTS

| 699724 | 12/1964 | Canada | 356/30 |
| 1958962 | 2/1967 | Fed. Rep. of Germany | |
| 7016584 | 4/1970 | Fed. Rep. of Germany | |
| 1403557 | 8/1975 | United Kingdom | |

Primary Examiner—F. L. Evans
Attorney, Agent, or Firm—Toren, McGeady and Goldberg

[57] ABSTRACT

A device for judging precious stones such as diamonds with ease, especially enables judgment of quality of cut, clarity or existence of imperfections and color grade of diamonds without requiring expert skill or experience. The device body (1) is provided with a window (3) at its upper part and light source (2) at its lower part. A plate (4) for supporting precious stones such as diamonds, is slidably inserted and carried between the window (3) and the light source (2). A base plate (14) which is slidably secured, is also provided to the device body (1), and a magnifying glass (12) for presenting precious stones in enlargement through the window (3), is fixed to the base plate (14). On the object lens side of the magnifying glass (12) is mounted a disc (17) having a small hole (18). The exterior of the disc (17) is colored in red or silver.

3 Claims, 11 Drawing Figures

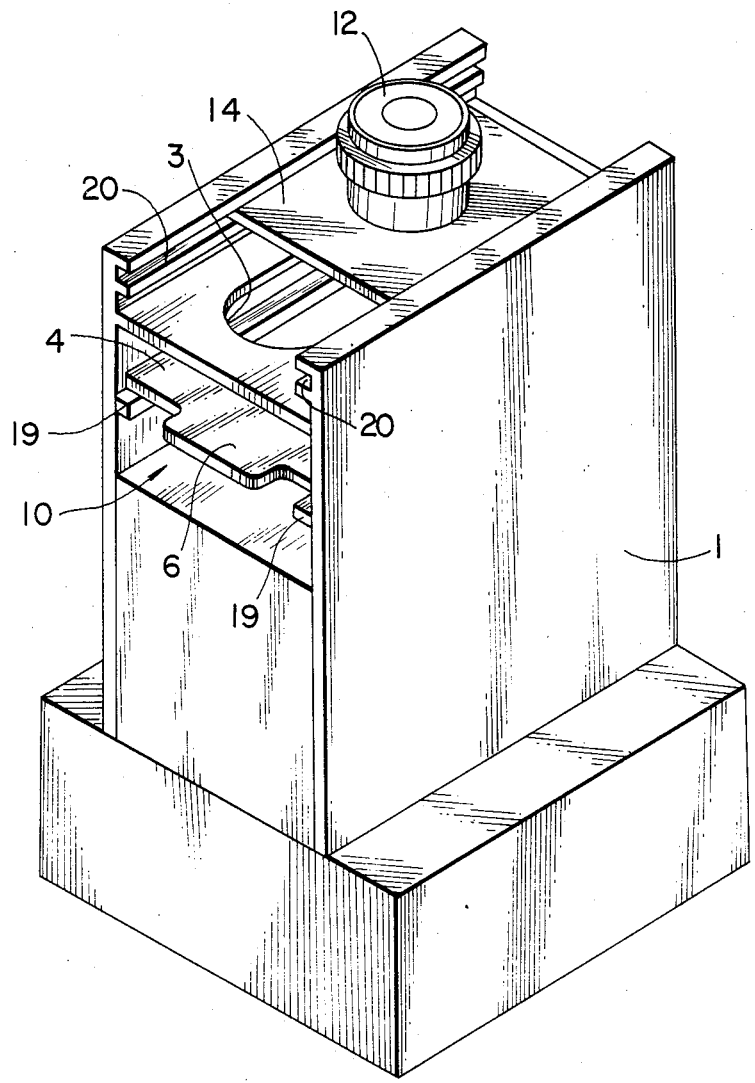

DEVICE FOR JUDGING BRILLIANCY OF PRECIOUS STONES SUCH AS DIAMONDS OR THE LIKE

FIELD OF THE INVENTION

The present invention relates to a device for judging quality of precious stones, particularly diamonds, and more especially relates to a device which enables common customers who are without professional knowledge of precious stones to easily judge the grade of the stones.

BACKGROUND OF THE INVENTION

It is needless to say that the value of a diamond lies in its weight or carat, but its cut, transparency, clarity and color are also important factors in judging its value.

Conventionally there have been Quality Analyses made out by professionals for indicating the value of a diamond. Common customers have been only to learn how to look at and read such Analyses, and it has been difficult for them to actually ascertain diamond articles with their own eyes, because such articles must be handled very carefully as, for instance they could easily slip and pop away when they are held by a pair of pincers. Moreover, there are many problems which are yet to be solved for creating the suitable environment to examine diamond articles such as preparing the desired light source and so on.

The present invention concerns a device of a simple structure which enables easy judgment of the cut, transparency, clarity and color of diamond articles. Moreover, with this device, diamond articles can be securely supported, and it is possible to easily compare the diamond article to be judged with the master stone. Further, the device does not require a special place, and can be easily employed at jewelry shops.

DISCLOSURE OF THE INVENTION

The present invention relates to a judging device which comprises a device body which slidably carries a plate which supports precious stones such as diamonds between a window on the upper part of the body and light source on the lower part, and a magnifying glass fixed to a sliding base plate which is secured to the device body. A disc having a small hole at its center, is mounted on the object lens side of the magnifying glass, and the exterior of the disc is of the color of red, silver or the like.

The device enables to clearly identify grade of cut, clarity and color of precious stones such as diamonds when they are seen through the object lens.

BRIEF DESCRIPTION OF THE DRAWINGS

FIG. 8 is a perspective view of another embodiment in which the supporting plate and the magnifying glass are supported in the horizontal direction.

DESCRIPTION OF PREFERRED EMBODIMENTS

In order to describe the present invention in more detail, an explanation of the attached drawings will be given below.

Figure 1:
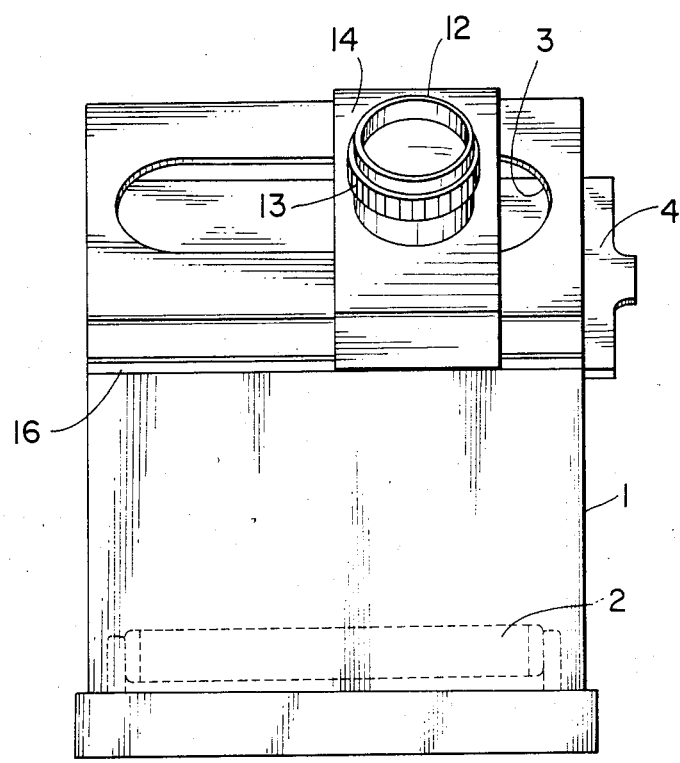
FIG. 1 is a front view.
Figure 4:
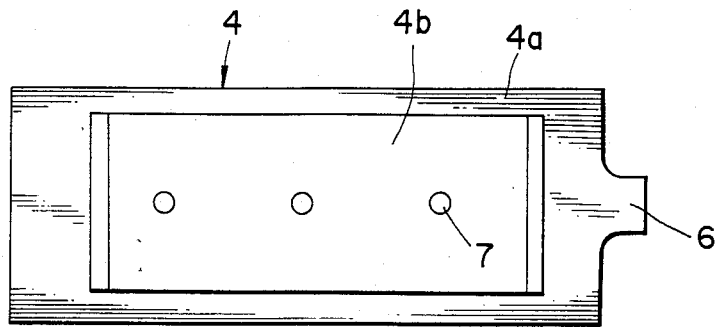
FIGS. 4 and 5 are plan views of the supporting plate.
Figure 5:
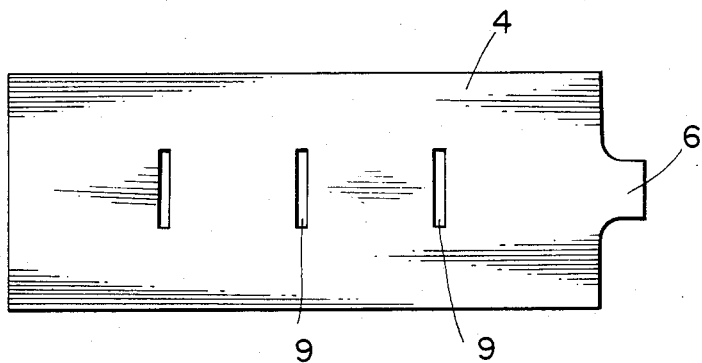
Figure 7:
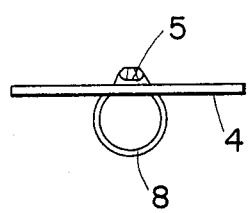
FIGS. 6 and 7 are side views of the supporting plate in the condition supporting a precious stone.
Figure 6:
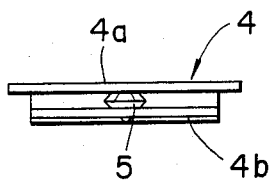

As shown in FIG. 1, a device body 1 is made like a box, and it is provided with light source (fluorescent light) 2 at its lower part and an oval window 3 at its upper part. A plate 4 made of transparent glass or acrylic plate, supports precious stones such as diamonds or the like. As shown in FIGS. 4 and 5, the plate is provided with a handle 6. The supporting plate 4 shown in FIG. 4 is comprised of two plates 4a, 4b as shown in FIG. 6 so that the tip of a diamond is secured in a small hole 7 of the plate 4b. The plate 4 in FIG. 5 is for supporting a ring 8, and a plurality of narrow slots 9 are provided for this purpose.

The supporting plate 4 is inserted in the device body 1 by placing both ends of the plate in notches 11, 11 provided at both sides of a side opening 10 provided between the window 3 and the light source 2 of the device body 1. In the present embodiment the notches are arranged in two rows one on top of the other, but it is of course not limited to this arrangement. It will be sufficient so long as the supporting plate 4 can be slided below the window 3 for its insertion and removal.

A magnifying glass 12 is provided with a focus adjustment ring 13, and is fixed to a base plate 14 by screwing or the like. Flanges 15 on both ends of the base plate 14 are engaged in grooves 16, and the plate 14 is arranged slidable in the londitudinal direction. A disc 17 having a small hole 18 at its center, is provided on the object lens side of the magnifying glass 12. It is desirable that the exterior of the disc 17 is colored in red, silver or the like and its interior or the lens side in black.

In another embodiment shown in FIG. 8, the supporting plate 4 and the plate 14 to which the magnifying glass 12 is fixed, are carried by the device body in the horizontal direction, but its basic structure is unchanged from the first embodiment.

Figure 2:
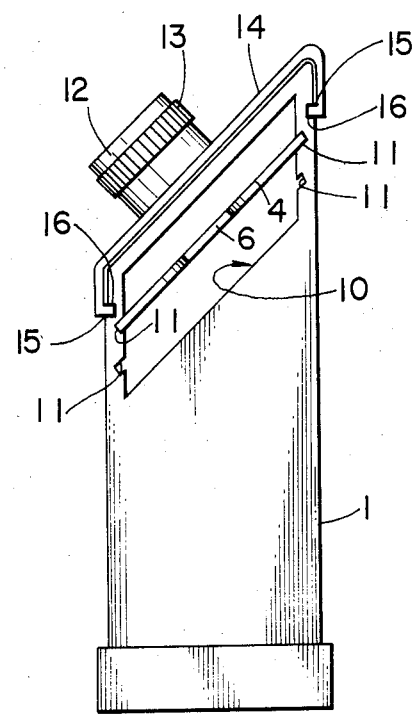
FIG. 2 is a side view.
Figure 3:
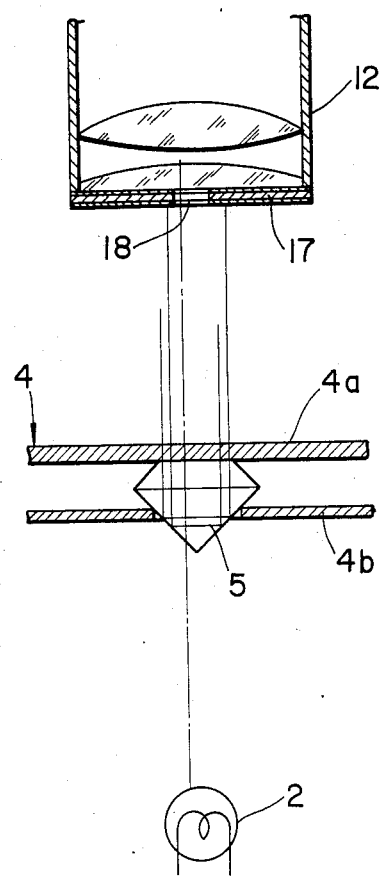
FIG. 3 is a view showing the principle of the invention.

It is different from the embodiment shown in FIGS. 1 and 2 in that when inserting the supporting plate 4 in the opening 10 on the side of the device body 1 between the window 3 and the light source, protrusions 19 are provided in place of the notches, and sliding of the base plate 14 to which the magnifying glass 12 is fixed, above the window of the device body 1, is carried out by inserting both edges of the base plate 14 in the grooves 20 provided in the device body 1.

Figure 9:
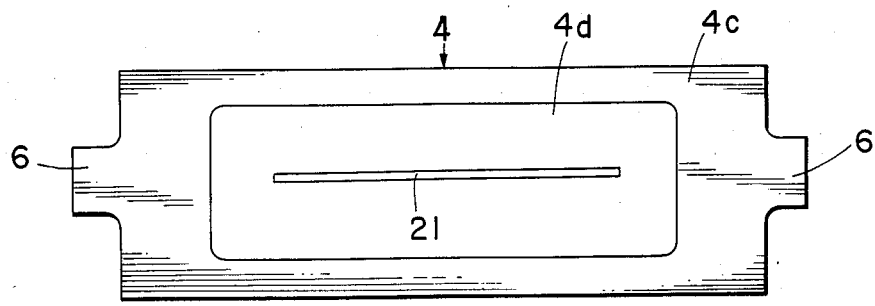
FIG. 9 is a plan view of a supporting plate suitable for judging the color of precious stones.
Figure 10:
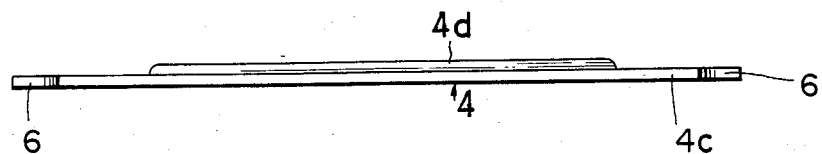
FIG. 10 is a side view thereof.
Figure 11:
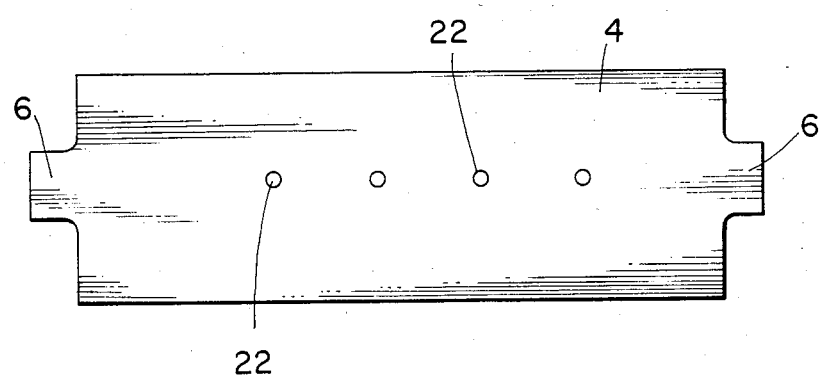
FIG. 11 is a plan view of a supporting plate having a conical concave part.

FIGS. 9 and 10 are a plan view and a side view respectively of a supporting plate especially suitable for judging the color of precious stones. An upper plate 4d of white acrylic material is attached to the center of the upper surface of the main body 4c of the supporting plate of transparent acrylic material. The upper plate 4d is provided with a horizontal groove 21 for placing a diamond article towards the side surface. The supporting plate 4 shown in FIG. 11 is simply provided with a plurality of conical dents 22 so that lower tips of diamond articles can be inserted therein.

With the structure of the present invention as described above, when the diamond 5 is seen through the magnifying glass 12 with the light from the light source 2, the color of the colored part of the disc 17 is reflected on the diamond, and the color reflected from the diamond can be seen through the magnifying glass. In case the color red is employed, the diamond which presents more red light, has more reflecting light, and therefore it is the diamond of better brilliance. On the other hand, if more white part is seen, it means that the light from the light source 2 passes through the magnifying glass 12 as it is, and thus the tested diamond can be judged as an article of inferior brilliance. The present device, thus, mainly enables examination and judgment of the quality of cut and grade of clarity. Also, if the supporting plate shown in FIG. 10 and the disc which is mounted on the object lens side of the magnifying glass, whose exterior is colored in silver are employed, the color of diamonds can be identified.

In this case, if a plurality of diamonds are placed on the supporting plate, and the diamond to be judged is compared with the one of excellent cut and high grade clarity, it is easier to judge its quality. Particularly, when the color of a diamond is to be judged, its grade can be determined by employing master stones varying from "D"–"Z" (no color to yellow).

INDUSTRIAL APPLICABILITY OF THE INVENTION

As described above, the present invention enables judgment of brilliance, grades of cut, clarity and color, respectively of precious stones especially diamonds without help of specialists, facilitating common consumers to select articles accurately and easily, and thus providing remarkably useful in sales of this kind of expensive articles.

What is claimed is:

1. A device for judging brilliancy of precious stones such a diamonds comprising a box-like device body having a first side and an opposite second side, disposed in spaced relation, said device body having a side opening located between said first and second sides, a plate arranged to support precious stones is slidably insertable through said side opening and is supported within said device body between said first and second sides, said device body having a window in the first side thereof, a light source located within said device body with said plate being locatable between said window and light source, a base plate slidably secured to said device body and extending over said first side transversely of said window, a magnifying glass mounted on said base plate and arranged to provide viewing through said window for magnifying and inspecting precious stones mounted on said plate within said device body, said magnifying glass has an object lens side facing said plate, a disc having a small hole therethrough being mounted on the object lens side of said magnifying glass, said disc having a first side facing said plate and an oppositely directed second side, and said first side of said disc being colored for reflecting the color thereof onto the precious stone on said plate so that the reflected color can be viewed through said magnifying glass.

2. A device, as set forth in claim 1, wherein said plate has a number of spaced openings therethrough.

3. A device, as set forth in claim 1, wherein said plate comprises a main body formed of a transparent plate and a white plate fixed to the center of said main body and facing toward the first side of said device body and said white plate having a groove for receiving precious stones to be inspected.

* * * * *